(12) United States Patent
Nagashima et al.

(10) Patent No.: US 9,904,226 B2
(45) Date of Patent: Feb. 27, 2018

(54) OPTICAL APPARATUS AND IMAGE FORMING APPARATUS INCLUDING THE OPTICAL APPARATUS

(71) Applicant: CANON KABUSHIKI KAISHA, Tokyo (JP)

(72) Inventors: Satoru Nagashima, Kawasaki (JP); Masayuki Sakai, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/429,055

(22) Filed: Feb. 9, 2017

(65) Prior Publication Data

US 2017/0153569 A1 Jun. 1, 2017

Related U.S. Application Data

(63) Continuation of application No. 14/962,091, filed on Dec. 8, 2015, now Pat. No. 9,606,487.

(30) Foreign Application Priority Data

Dec. 10, 2014 (JP) .................................. 2014-250410

(51) Int. Cl.
G03G 15/00 (2006.01)
G03G 15/04 (2006.01)
G02B 5/00 (2006.01)

(52) U.S. Cl.
CPC ......... *G03G 15/5058* (2013.01); *G02B 5/003* (2013.01); *G03G 15/0409* (2013.01);
(Continued)

(58) Field of Classification Search
CPC ......... G01N 24/474; G01N 2201/0642; G03G 15/0827; G03G 15/5033; G03G 15/5041; G03G 15/5058; G03G 2215/00042
See application file for complete search history.

(56) References Cited

U.S. PATENT DOCUMENTS 4,989,985 A * 2/1991 Hubble, III ............ G01N 21/55
250/341.8
5,946,554 A * 8/1999 Echigo ................ H01L 23/3121
257/E21.505
(Continued)

FOREIGN PATENT DOCUMENTS

CN 103308422 A 9/2013
JP 09153678 A * 6/1997
(Continued)

*Primary Examiner* — Carla Therrien
(74) *Attorney, Agent, or Firm* — Canon U.S.A. Inc., IP Division

(57) ABSTRACT

To prevent the detection accuracy from deteriorating due to stray light, an optical apparatus includes the following configuration. The optical apparatus includes a light-emitting member, a light-receiving member, and a substrate on which the light-emitting member and the light-receiving member are mounted. The substrate includes a plate-like substrate layer and a plate-like conductive layer. The optical apparatus further includes a light-shielding member disposed between the light-receiving member and the light-emitting member and inserted in a through-hole of the substrate provided between the light-receiving member and the light-emitting member. The light-receiving member receives reflected light from a portion to be irradiated with the light emitted from the light-emitting member. The conductive layer is excellent in light-shielding property compared to the substrate layer. The conductive layer is exposed to an inner cylindrical surface of the through-hole.

20 Claims, 9 Drawing Sheets

(52) U.S. Cl.
CPC ..... *G03G 15/5041* (2013.01); *G03G 15/5062* (2013.01); *G01N 2201/0642* (2013.01); *G03G 2215/00042* (2013.01); *G03G 2215/00616* (2013.01)

(56) References Cited

U.S. PATENT DOCUMENTS

| | | | | |
|---|---|---|---|---|
| 6,740,862 | B2* | 5/2004 | Paritsky | H04R 23/008 250/216 |
| 8,677,605 | B2* | 3/2014 | Lim | H03K 17/941 250/216 |
| 2003/0059178 | A1* | 3/2003 | Kobayashi | G02B 6/4206 385/94 |
| 2004/0065894 | A1* | 4/2004 | Hashimoto | H01L 33/642 257/100 |
| 2009/0095881 | A1* | 4/2009 | Funakubo | G01J 1/24 250/205 |
| 2011/0204233 | A1* | 8/2011 | Costello | G01S 7/4813 250/338.4 |
| 2012/0160994 | A1* | 6/2012 | Costello | G01D 11/245 250/221 |
| 2013/0272740 | A1* | 10/2013 | Nakagawa | G01N 21/55 399/74 |

FOREIGN PATENT DOCUMENTS

| | | | | | |
|---|---|---|---|---|---|
| JP | 2001242348 | A | * | 9/2001 | |
| JP | 2004214059 | A | * | 7/2004 | |
| JP | 2005024459 | A | * | 1/2005 | |
| JP | 2006-267644 | A | | 10/2006 | |
| JP | 2009058520 | A | * | 3/2009 | |
| JP | 2013191835 | A | * | 9/2013 | ............. G01N 21/55 |

* cited by examiner

OPTICAL APPARATUS AND IMAGE FORMING APPARATUS INCLUDING THE OPTICAL APPARATUS

CROSS-REFERENCE TO RELATED APPLICATIONS

This application is a continuation of U.S. Pat. application Ser. No. 14/962,091 filed Dec. 8, 2015, which claims the benefit of Japanese Patent Application No. 2014-250410, filed Dec. 10, 2014, the disclosures of each of which are hereby incorporated by reference herein in their entirety.

BACKGROUND OF THE INVENTION

Field of the Invention

The present invention relates to an optical apparatus that receives light reflected from a target portion when the target portion is irradiated with the light and also relates to an image forming apparatus, such as a copying machine, a printer, or a facsimile machine, which includes the optical apparatus.

Description of the Related Art

In general, an image forming apparatus is sensitive to an operating environment and various conditions (e.g., the number of sheets to be printed) because the density of each color is variable and the tint of a formed image is variable too. A color image forming apparatus is configured to overlap a plurality of color images to form a composite color image. Therefore, positional deviation tends to occur in respective color images. For example, when the color image forming apparatus includes four-color (e.g., yellow, magenta, cyan, and black) photosensitive drums, the relative position between two of four-color images is variable.

There is a conventional method for correcting the positional deviation of each color or each color density. More specifically, the conventional method includes causing a light-receiving member of an optical apparatus to detect the amount of light reflected from a patch (i.e., a reference pattern) formed on an intermediate transfer member, a photosensitive member, or a sheet. The method includes calculating a positional deviation between respective colors and a density variation of each color based on a detection result representing the amount of received light. The method includes controlling various image forming conditions based on the calculation result in such a way as to appropriately adjust the positional deviation between respective colors and the density of each color.

As discussed in Japanese Patent Application Laid-Open No. 2013-191835, there is a conventionally known configuration capable of improving the detection accuracy of an optical apparatus (e.g., an optical sensor) that is used in the above-mentioned patch detection.

The optical apparatus discussed in Japanese Patent Application Laid-Open No. 2013-191835 includes a light-emitting member and a light-receiving member mounted on a substrate and covered with a housing that serves as a light-shielding member. However, according to such a conventional arrangement, the detection accuracy may deteriorate due to stray light. Therefore, the present invention intends to prevent the detection accuracy from being deteriorated by the stray light.

SUMMARY OF THE INVENTION

According to an aspect of the present invention, an optical apparatus includes a light-emitting member, a light-receiving member, a substrate including a plate-like substrate layer and a plate-like conductive layer, on which the light-emitting member and the light-receiving member are mounted, and a light-shielding member disposed between the light-receiving member and the light-emitting member and inserted in a through-hole of the substrate provided between the light-receiving member and the light-emitting member. The light-receiving member is configured to receive reflected light from a portion to be irradiated with the light emitted from the light-emitting member. The conductive layer is excellent in light-shielding property compared to the substrate layer. The conductive layer is exposed to an inner cylindrical surface of the through-hole.

Further features of the present invention will become apparent from the following description of exemplary embodiments with reference to the attached drawings.

DESCRIPTION OF THE EMBODIMENTS

[Image Forming Apparatus]

Figure 1:
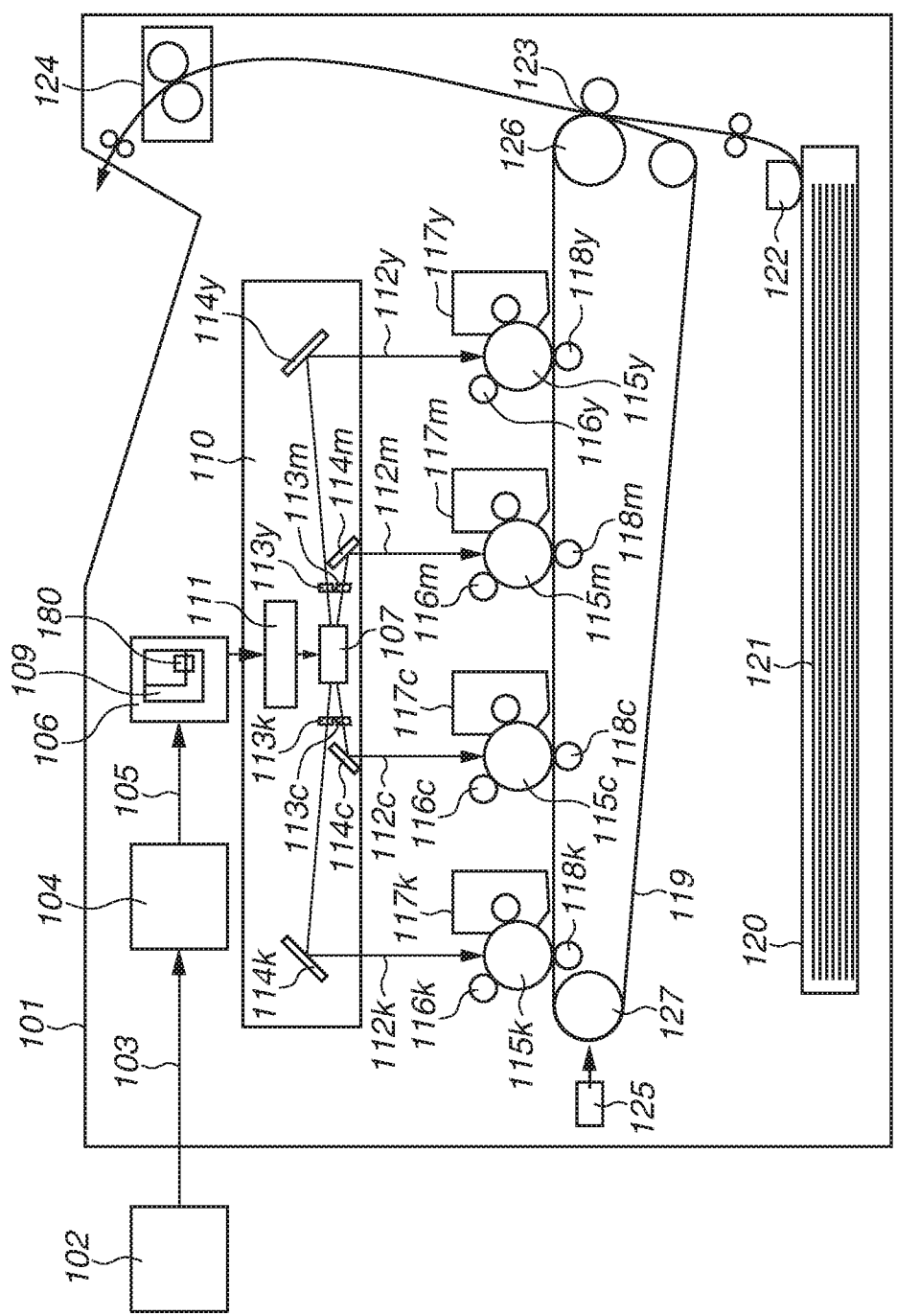
FIG. 1 is a schematic configuration illustrating an image forming apparatus.

A first exemplary embodiment will be described in detail below. FIG. 1 is a schematic cross-sectional view illustrating a configuration of a color laser printer, which is an image forming apparatus according to the present invention. The image forming apparatus according to the present invention includes four-color image forming units to form a composite color image by overlapping four-color images. For example, the combination of four colors is yellow (Y), magenta (M), and cyan (C) of chromatic color developers and black (Bk) of an achromatic color developer. A color laser printer 101 is an image forming apparatus that can receive image data 103 from a host computer 102. The color laser printer 101 includes a print image generation unit 104 that can develop image data into desired video signal format data to generate an image forming video signal 105. An image forming control unit 106 includes a central processing unit 109 (hereinafter, simply referred to as CPU 109) that is operable as a control unit. The video signal generated by the print image generation unit 104 can be transmitted to the image forming control unit 106 from the print image generation unit 104. The image forming control unit 106 drives a plurality of laser diodes 111 provided in a scanner unit 110 according to the video signal. Each laser diode 111 serves as a laser emitting element. The scanner unit 110 is operable as an exposure unit. Respective photosensitive drums 115y, 115m, 115c, and 115k (hereinafter, collectively referred to as "photosensitive drum 115") are irradiated with laser beams 112y, 112m, 112c, and 112k (hereinafter, collectively referred to as "laser beam 112") emitted from respective laser diodes and traveling via a polygon mirror 107, lenses 113y, 113m, 113c, and 113k (hereinafter, collectively referred to as "lens 113"), mirrors 114y, 114m, 114c, and 114k (hereinafter, collectively referred to as "mirror 114"). Respective charging units 116y, 116m, 116c, and 116k (hereinafter, collectively referred to as "charging unit 116") can charge the corresponding photosensitive drums 115 to have a desired electric charge amount. When the surface of each photosensitive drum 115 is irradiated with the laser beam 112, an electrostatic latent image can be formed at an irradiated portion where the electric potential decreases. To visualize the electrostatic latent image formed on the photosensitive drum 115 irradiated with the laser beam, respective developing units 117y, 117m, 117c, and 117k (hereinafter, collectively referred to as "developing unit 117") can form a toner image reflecting the electrostatic latent image on the photosensitive drum 115. Respective primary transfer members 118y, 118m, 118c, and 118k (hereinafter, collectively referred to as "primary transfer member 118") can primarily transfer the toner images formed on respective photosensitive drums onto an endless belt (hereinafter, referred to as "intermediate transfer belt") 119. In this respect, each primary transfer member 118 serves as a transfer unit to which a transfer voltage is applied. In the primary transfer operation, a yellow image is initially transferred onto the intermediate transfer belt 119. Then, magenta, cyan, and black images are sequentially transferred onto the intermediate transfer belt 119, in such a way as to form a composite color image. In this case, the intermediate transfer belt 119 carries a four-color toner image. The intermediate transfer belt 119 is rotatably engaged with a tension roller 127 and a driving roller 126. The driving roller 126 can control the conveyance of the intermediate transfer belt 119. A paper feeding roller 122 is located adjacently to a cassette 120. The paper feeding roller 122 conveys each recording paper 121 from the cassette 120 toward a secondary transfer portion 123 in such a way as to be synchronized with the image primarily transferred on the intermediate transfer belt 119. The color laser printer 101 performs a secondary transfer operation at the secondary transfer portion 123 so that the image can be transferred to the recording paper 121. In this case, an appropriate bias voltage is applied to a secondary transfer roller to increase transfer efficiency. A fixing device 124 performs a thermal fixing operation by applying heat and pressure to the recording paper on which the image has been secondarily transferred. A stable color image can be fixed on the recording paper. Then, the recording paper can be discharged via a discharge portion. An optical sensor unit 125 is operable as a detection unit and is supported by the tension roller 127. The optical sensor unit 125 is an optical sensor capable of detecting a positional deviation correction pattern and a density correction pattern that are used to detect a positional deviation amount and a density variation of each color image transferred on the intermediate transfer belt 119. At desired timing, the optical sensor unit 125 detects the position of the correction pattern of each color formed on the intermediate transfer belt 119 and a difference from a target density. Then, the optical sensor unit 125 outputs the detection result to the CPU 109 (i.e., the control unit). The CPU 109 saves the detection result in a random access memory 180 (hereinafter, simply referred to as RAM 180), which is a storage unit. The saved detection result can be fed back to the image forming control unit 106. The image forming control unit 106 can correct the positional deviation of each color toner image in a main scanning direction and a sub scanning direction. Further, the image forming control unit 106 can correct the density of each color.

[Optical Sensor Unit]

Figure 2:
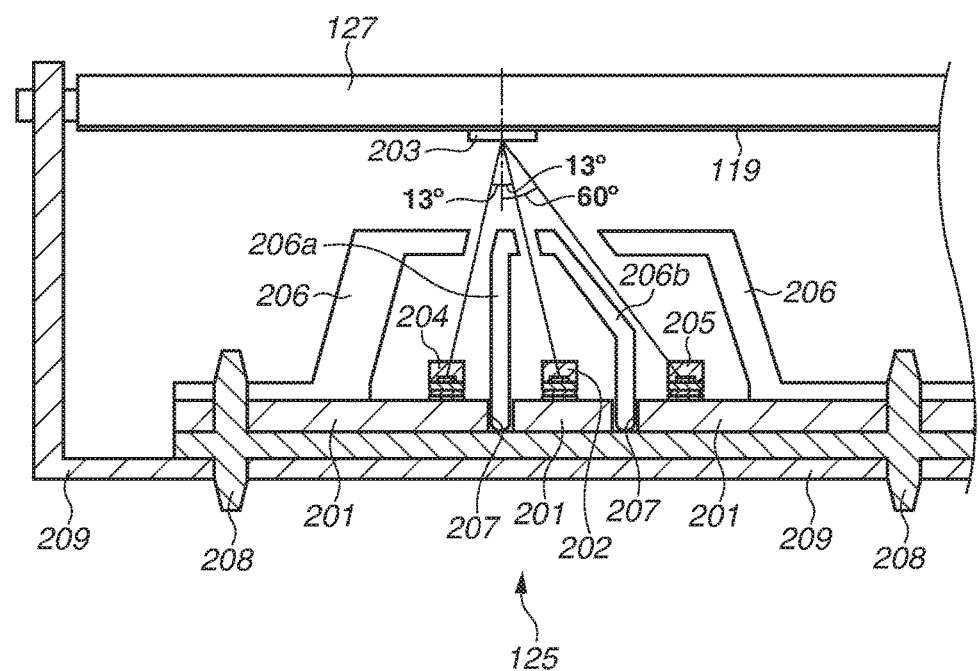
FIG. 2 is a schematic cross-sectional view illustrating an optical sensor unit.

Next, the optical sensor unit 125, which is operable as an optical apparatus, will be described in detail below. FIG. 2 is a schematic cross-sectional view illustrating the optical sensor unit 125. A light-emitting member 202 is an LED infrared light-emitting element. Hereinafter, the light-emitting member 202 is referred to as "light-emitting element 202." Two light-receiving members 204 and 205 are phototransistor infrared light-receiving elements. The light-receiving member 205 can receive diffuse-reflected light of the light-emitting element 202. The light-receiving member 204 can receive mirror surface reflected light (regular reflected light). Hereinafter, the light-receiving members 204 and 205 are referred to as light-receiving elements 204 and 205, respectively. A substrate 201 has a surface on which the light-emitting element 202, respective light-receiving elements 204 and 205, and electronic circuit components (not illustrated) are mounted. Each of the light-emitting element 202 and the respective light-receiving elements 204 and 205 is a bare chip element, which is mounted on the substrate 201 in such a manner that a central axis thereof extends in a direction substantially perpendicular to the surface of the substrate 201.

A through-hole 207 is provided between the light-emitting element 202 and light-receiving element 204. Another through-hole 207 is provided between the light-emitting element 202 and the light-receiving element 205. Each through-hole 207 extends from the front surface to the back surface of the substrate 201 in a direction perpendicular to the surface of the substrate 201. A resin-made housing member 206 (hereinafter, referred to as "housing 206") has a portion that covers the light-emitting element 202 and a diaphragm aperture through which the light emitted from the light-emitting element 202 can pass, a portion that covers the light-receiving element 204, a diaphragm aperture through which light can enter the light-receiving element 204, a portion that covers the light-receiving element 205, and a diaphragm aperture through which light can enter the light-receiving element 205. When the light-emitting element 202 emits light, a beam travels through the diaphragm aperture of the housing 206 formed at the region that covers the light-emitting element 202. In this case, the surface of the intermediate transfer belt 119 can be irradiated with the beam that inclines by an angle of 13° relative to a direction perpendicular to the surface of the intermediate transfer belt 119. On the other hand, the light-receiving element 204 can receive light reflected from the surface of the intermediate transfer belt 119 by an angle of 13° relative to the direction perpendicular to the surface of the intermediate transfer belt 119 and passing through the diaphragm aperture of the housing 206 formed at the region that covers the light-receiving element 204. Similarly, the light-receiving element 205 can receive light reflected from the surface of the intermediate transfer belt 119 by an angle of 60° relative to the direction perpendicular to the surface of the intermediate transfer belt 119 and passing through the diaphragm aperture of the housing 206 formed at the region that covers the light-receiving element 205. The housing 206 includes two wall portions 206a and 206b inserted in corresponding through-holes 207. One wall portion 206a is disposed between the light-emitting element 202 and the light-receiving element 204. The other wall portion 206b is disposed between the light-emitting element 202 and the light-receiving element 205.

A sensor stay (stay member) 209 is a positioning member that supports the optical sensor unit 125 to the tension roller 127 at a position where a predetermined distance can be kept between the optical sensor unit 125 and the intermediate transfer belt 119. The sensor stay 209 is a plate-like metal member. A spacer member (hereinafter, simply referred to as "spacer") 208 is disposed between the substrate 201 and the sensor stay 209 in such a way as to prevent any interference with electronic components (not illustrated) provided on the substrate 201. The spacer 208 is opposed to the back surface of the substrate 201, while the light-emitting element 202 and the light-receiving elements 204 and 205 are mounted on the front surface of the substrate 201. The spacer 208 is a resin-made member, which has a black surface that faces the back surface of the substrate 201. The black surface can absorb the light from the light-emitting element 202. Further, the surface of the spacer 208 is a matt finished surface capable of diffusing and reflecting stray light having not been absorbed. The spacer 208 includes boss portions by which the substrate 201, the housing 206, and the sensor stay 209 are positioned with each other in a predetermined relationship. The above-mentioned members are united tightly by means of screws (not illustrated), as the optical sensor unit 125, and are brought into contact with and attached to a bearing portion of the tension roller 127. A toner pattern 203, which is carried by the intermediate transfer belt 119, is a portion to be irradiated with light. When infrared light is emitted from the light-emitting element 202, the light-receiving element 204 receives mirror surface reflected light from the surface of the intermediate transfer belt 119 and the positional deviation and density variation detecting toner pattern 203 transferred onto the intermediate transfer belt 119. The light-receiving element 205 receives diffuse-reflected light. Therefore, it is feasible to detect a positional deviation amount of the positional deviation and density variation detecting toner pattern 203 and a density variation amount from a desired density.

Figure 3:
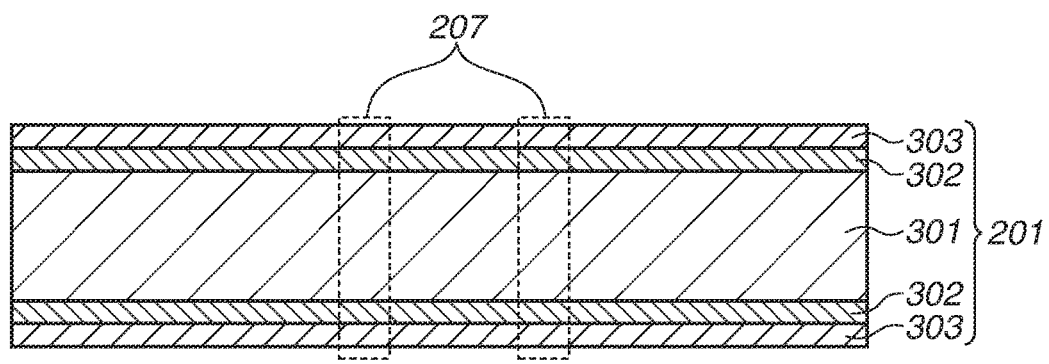
FIG. 3 is a cross-sectional view of a substrate in a state where there is not any through-hole formed therein.

FIG. 3 is a cross-sectional view of the substrate 201 in a state where the through-hole 207 is not yet formed. The substrate 201 is composed of a substrate layer 301, two copper foil layers 302, and two solder resist layers 303. The substrate layer 301 is a glass epoxy resin-made member. Each copper foil layer 302 is a thin copper-made layer. One copper foil layer 302 is formed on the front surface of the substrate layer 301. The other copper foil layer 302 is formed on the back surface of the substrate layer 301. The copper foil layer 302 is excellent in light-shielding property compared to the substrate layer 301. As illustrated in FIG. 3, the copper foil layer 302 covers a region corresponding to the through-hole 207. The substrate layer 301, the copper foil layers 302, and the solder resist layers 303 are laminated layers that cooperatively constitute a plate-like configuration of the substrate 201.

Figure 4:
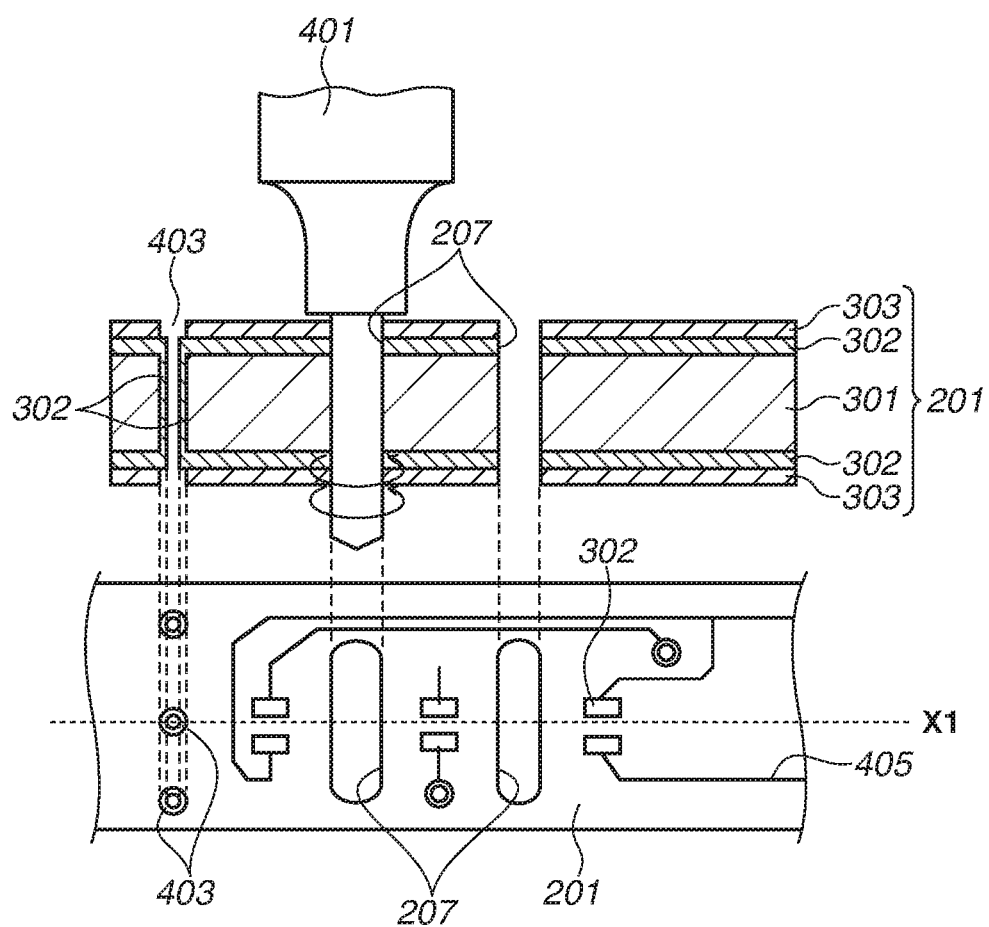
FIG. 4 is a cross-sectional view (an upper part of the drawing) and an upper surface view (a lower part of the drawing) of the substrate, which illustrates a formation of through-holes.

FIG. 4 is a set of a cross-sectional view (an upper part of the drawing) and an upper surface view (a lower part of the drawing) of the substrate 201, which illustrates a formation of the through-holes 207. The cross-sectional view illustrates a cross section taken along a dotted line X1 shown in the upper surface view. A drill 401 is a rotating tool that enables a user to perform a cutting work to open each through-hole 207 in the substrate 201. in the substrate 201, a place where the through-hole 207 can be opened with the drill 401 is a portion where the copper foil layer 302 is provided. Each through-hole 207 extends across the solder resist layers 303, the copper foil layers 302, and the substrate layer 301 vertically from the front surface to the back surface of the substrate 201. A through-hole via 403 extends from the front surface to the back surface of the substrate 201. The through-hole via 403 includes an inner cylindrical surface on which the copper foil layer 302 is formed. The copper foil layer 302 provided on the front surface of the substrate 201 and the copper foil layer 302 provided on the back surface are conductive layers electrically connected to each other and having the same potential (ground). A signal line (a circuit pattern) 405 is formed on the surface of the substrate 201 and is electrically connected to the light-emitting element 202, the light-receiving elements 204 and 205, the electronic circuit components (not illustrated), and the CPU 109 illustrated in FIG. 1.

Figure 5:
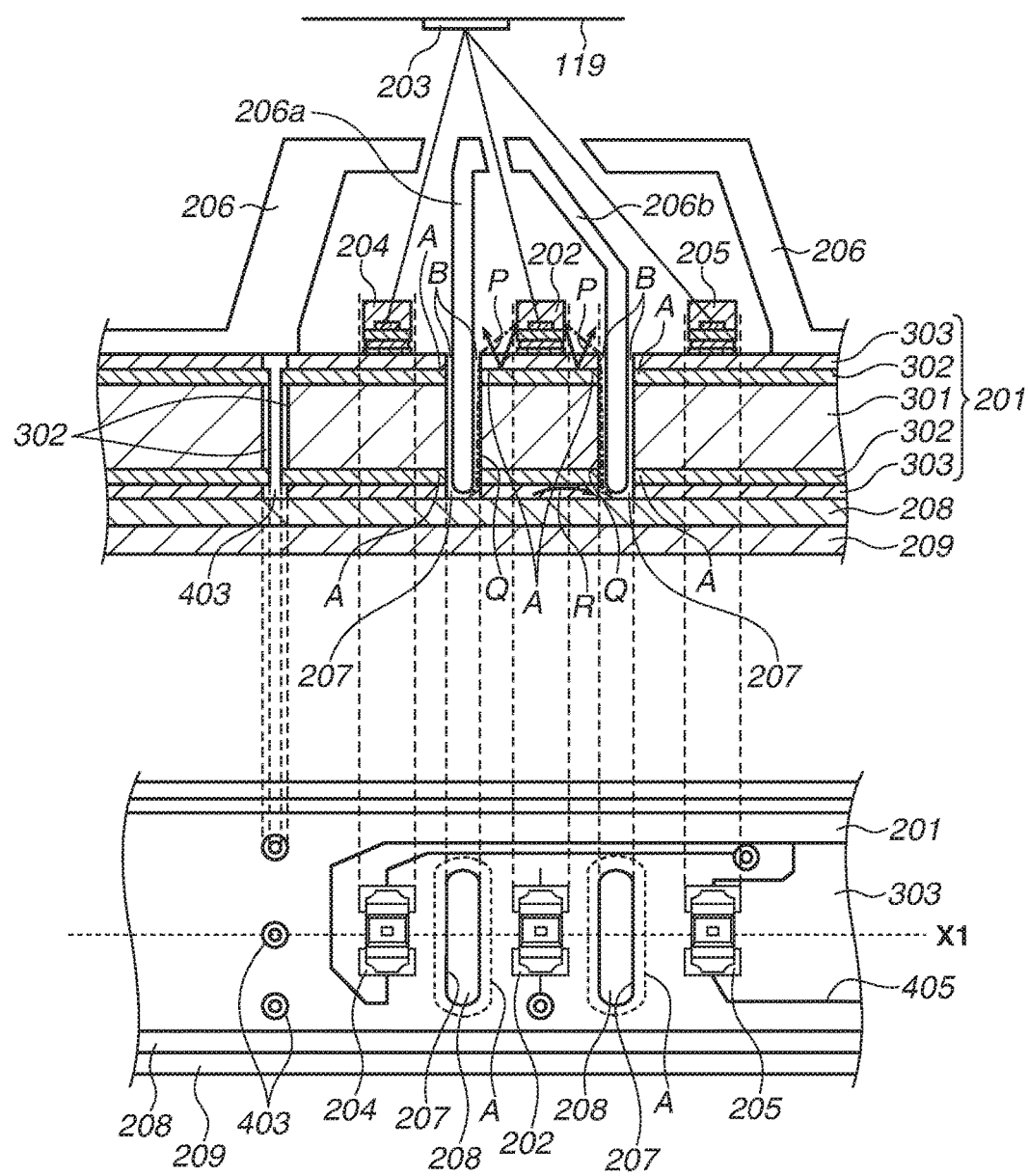
FIG. 5 is a cross-sectional view (an upper part of the drawing) and an upper surface view (a lower part of the drawing) of the optical sensor unit.

FIG. 5 illustrates a cross-sectional view (an upper part of the drawing) of the optical sensor unit 125 in a state where the light-emitting element 202 and the light-receiving elements 204 and 205 are mounted on the substrate 201 that includes the through-hole 207 formed therein and the housing 206 is attached to the substrate 201. FIG. 5 further illustrates an upper surface view (a lower part of the drawing) of the optical sensor unit 125 in a state where the housing 206 is not yet installed. The upper surface view of FIG. 5 illustrates an appearance of the optical sensor unit 125 seen from a direction perpendicular to the extending direction of the plate-like substrate 201 (i.e., an axial direction of the through-hole 207 perpendicular to the surface). The cross-sectional view of FIG. 5 illustrates a cross section taken along a dotted line X1 shown in the upper surface view. The light-emitting element 202 and the light-receiving elements 204 and 205 are mounted on the substrate 201 by reflowing. The housing 206 is attached to the substrate 201 via the through-holes 207. The substrate 201 and the sensor stay 209 are mutually positioned with the boss portions of the spacer 208. Then, these members are united tightly by means of screws (not illustrated). A region where the copper foil layer 302 is provided covers the mounting positions of the light-emitting element 202 and the light-receiving elements 204 and 205 and each region A surrounding the through-hole 207. The copper foil layer 302 extends along an inner cylindrical surface of the through-hole 207. A cross section of the copper foil layer 302 is exposed to the inner cylindrical surface of the through-hole 207.

As indicated by a path P, the light emitted from the light-emitting element 202 is reflected by the copper foil layer 302 in the region A. In other words, the copper foil layer 302 prevents the emitted light from entering the substrate layer 301. Because unnecessary light is prevented from entering the substrate layer 301, the light emitted from the light-emitting unit can be prevented from becoming disturbance light that travels in the substrate and reaching the light-receiving elements 204 and 205. Further, as indicated by a path R, disturbance light having entered via a clearance between the substrate 201 and the spacer 208 is reflected by the copper foil layer 302 in the region A. In other words, the copper foil layer 302 prevents the disturbance light from entering the light-receiving elements 204 and 205. Further, as indicated by a path Q, light leaking from a clearance between the through-hole 207 and a light-shielding member 206 to the back surface of the substrate 201 is absorbed or diffuse-reflected by the front surface of the spacer 208. In other words, the spacer 208 can suppress the leaking light from reaching the light-receiving elements 204 and 205.

[Comparative Example]

Figure 9:
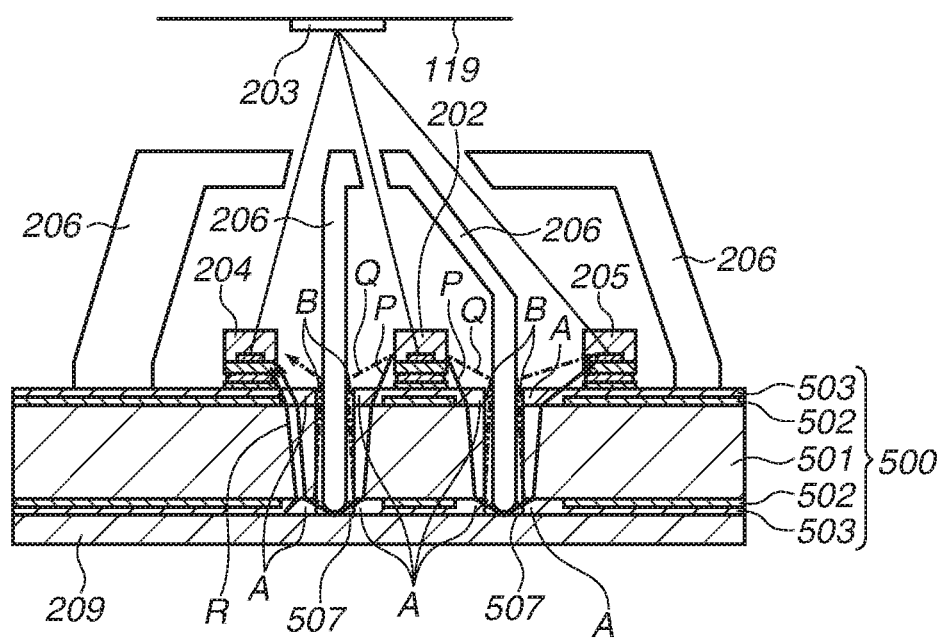
FIG. 9 is a cross-sectional view illustrating a comparative example of the optical sensor unit.

FIG. 9 is a cross-sectional view illustrating a comparative example of the optical sensor. A substrate 500 illustrated in FIG. 9 has front and back surfaces on which electronic components can be mounted. The substrate 500 is composed of a substrate layer 501, copper foil layers 502, and solder resist layer 503. The substrate layer 501 is a glass epoxy resin-made member. A light-emitting unit 202 and two light-receiving units 204 and 205 are fixed on the substrate 500 by surface mounting. Two through-holes 507 extend from the front surface to the back surface of the substrate 500. A light-shielding member 206 covers the light-emitting unit 202 and respective light-receiving units 204 and 205. A sensor stay 209 holds the substrate 500 and is attached to a detection target object.

The substrate 500 of the comparative optical sensor does not include the copper foil layer 502 in each region A adjacent to the corresponding through-hole 507. Further, as indicated by a region B, there is a clearance between the through-hole 507 and the light-shielding member 206. Therefore, as indicated by a path P, the light of the light-emitting unit 202 enters the substrate 500 via the through-hole 507 and a surrounding portion thereof where the copper foil layer 502 is not present. The sensor stay 209 reflects the light having entered the substrate 500. The reflected light can reach the light-receiving element. This is one reason why the output of the optical sensor changes undesirably. Further, as indicated by a path R, disturbance light having entered the substrate layer 501 travels and reaches the sensor stay 209. As indicated by a path Q, leaking light from a clearance between the through-hole 507 and the light-shielding member 206 also reaches the sensor stay 209. The sensor stay 209 reflects the disturbance light and leaking light. The reflected light can reach the light-receiving element. This is another reason why the output of the optical sensor changes undesirably. If the sensor output changes due to the disturbance light and the leaking light as mentioned above, the dynamic range of the optical sensor decreases undesirably. The dynamic range is a ratio of maximum output value to minimum output value of a target object to be detected. The detection accuracy of the optical sensor deteriorates according to the reduction of the dynamic range.

The present exemplary embodiment is different from the above-mentioned comparative example in the following features. The copper foil layer 502 is present in the region covering not only the mounting portions of the light-emitting element 202 and the light-receiving elements 204 and 205 but also the position substantially identical to the outer diameter of the through-hole 507. Therefore, it is feasible to prevent the stray light from entering the light-receiving elements 204 and 205 and suppress the detection accuracy of the optical sensor from deteriorating.

As mentioned above, according to the present exemplary embodiment, it is feasible to prevent the disturbance light having travelled in the substrate layer 301 from entering the light-receiving elements 204 and 205. Further, it is feasible to prevent the light leaking via the clearance between the light-shielding member 206 and the through-hole 207 from entering the light-receiving elements 204 and 205. Therefore, the optical sensor unit 125 can secure an adequate dynamic range (i.e., the ratio of maximum output value to minimum output value) in the detection of the positional deviation and density variation detecting toner patch (i.e., the reference pattern) 203. When the dynamic range is maintained adequately without causing undesirable reduction, the optical sensor unit 125 can accurately detect the positional deviation and density variation detecting toner patch (i.e., the reference pattern) 203. More specifically, the present exemplary embodiment brings an effect of suppressing the detection accuracy of the optical sensor unit 125 from deteriorating due to the stray light.

Figure 6:
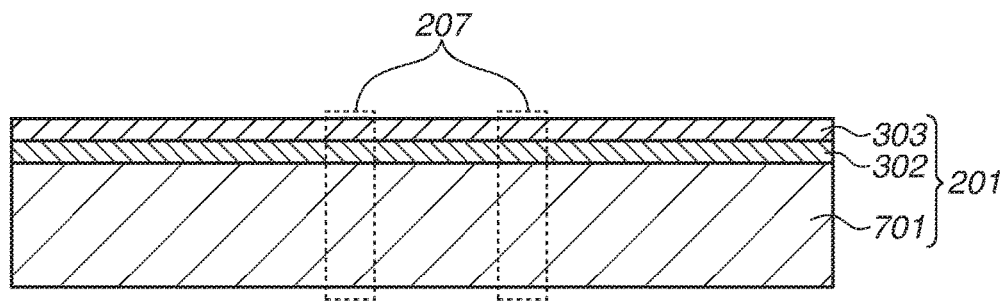
FIG. 6 is a cross-sectional view of a substrate in a state where there is not any through-hole formed therein.

A second exemplary embodiment will be described in detail below. As mentioned above, the method according to the first exemplary embodiment includes forming the through-holes 207 in the glass epoxy resin-made substrate 301 having front and back surfaces on which electronic components can be mounted with the drill 401. The second exemplary embodiment is different from the first exemplary embodiment in that the substrate 201 includes a paper phenol resin-made substrate layer 701 having only one surface on which electronic components can be mounted, as illustrated in FIG. 6. Further, the method according to the second exemplary embodiment includes performing a presswork to form the through-holes 207 with a die 801 in such a way as to extend across the substrate 201, as described in detail below with reference to FIG. 7. The remaining components are assigned the reference numerals already described in the first exemplary embodiment when these components are similar to those described in the first exemplary embodiment. Therefore, redundant description thereof will be avoided.

FIG. 6 is a cross-sectional view of the substrate 201 in a state where the through-holes 207 are not yet formed. The substrate 201 is composed of the substrate layer 701, the copper foil layer 302, and the solder resist layer 303. The substrate layer 701 is the paper phenol resin-made member. The copper foil layer 302 is provided on only one surface of the substrate layer 701. The copper foil layer 302 is excellent in light-shielding property compared to the substrate layer 701. The copper foil layer 302 covers a region corresponding to the through-hole 207.

Figure 7:
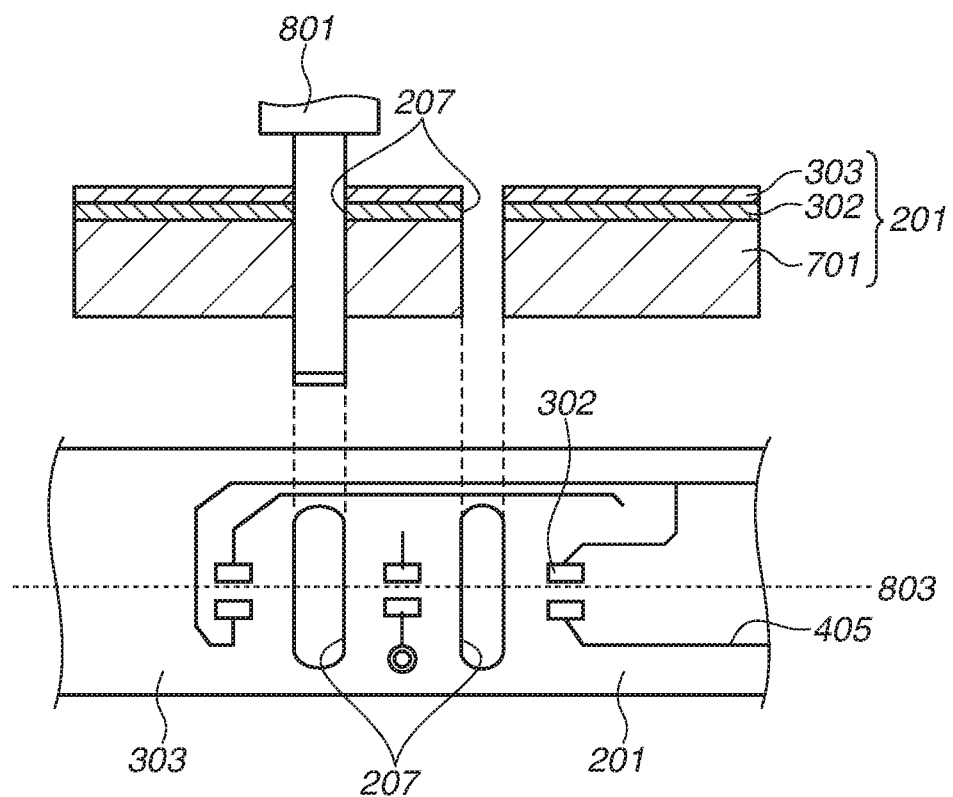
FIG. 7 illustrates a cross-sectional view (an upper part of the drawing) and an upper surface view (a lower part of the drawing) of the substrate, which illustrates a formation of through-holes.

FIG. 7 is a set of a cross-sectional view (an upper part of the drawing) and an upper surface view (a lower part of the drawing) of the substrate 201, which illustrates a formation of the through-holes 207. The cross-sectional view illustrates a cross section of the substrate 201 taken along a dotted line 803. The die 801 is a machining tool that is usable in a presswork to open the through-holes 207 in the substrate 201. Each through-hole 207 extends vertically across the solder resist layer 303, the copper foil layer 302, and the substrate layer 301 vertically from the front surface to the back surface of the substrate 201. The portion where the through-holes 207 are provided is a region where the copper foil layer 302 is present. Therefore, the copper foil layer 302 can be disposed in such a way as to cover the position substantially identical to the outer diameter of the through-hole 207. A signal line 405 is formed on the surface of the substrate 201 and is electrically connected to the light-emitting element 202, the light-receiving elements 204 and 205, the electronic circuit components (not illustrated), and the CPU 109 illustrated in FIG. 1.

Figure 8:
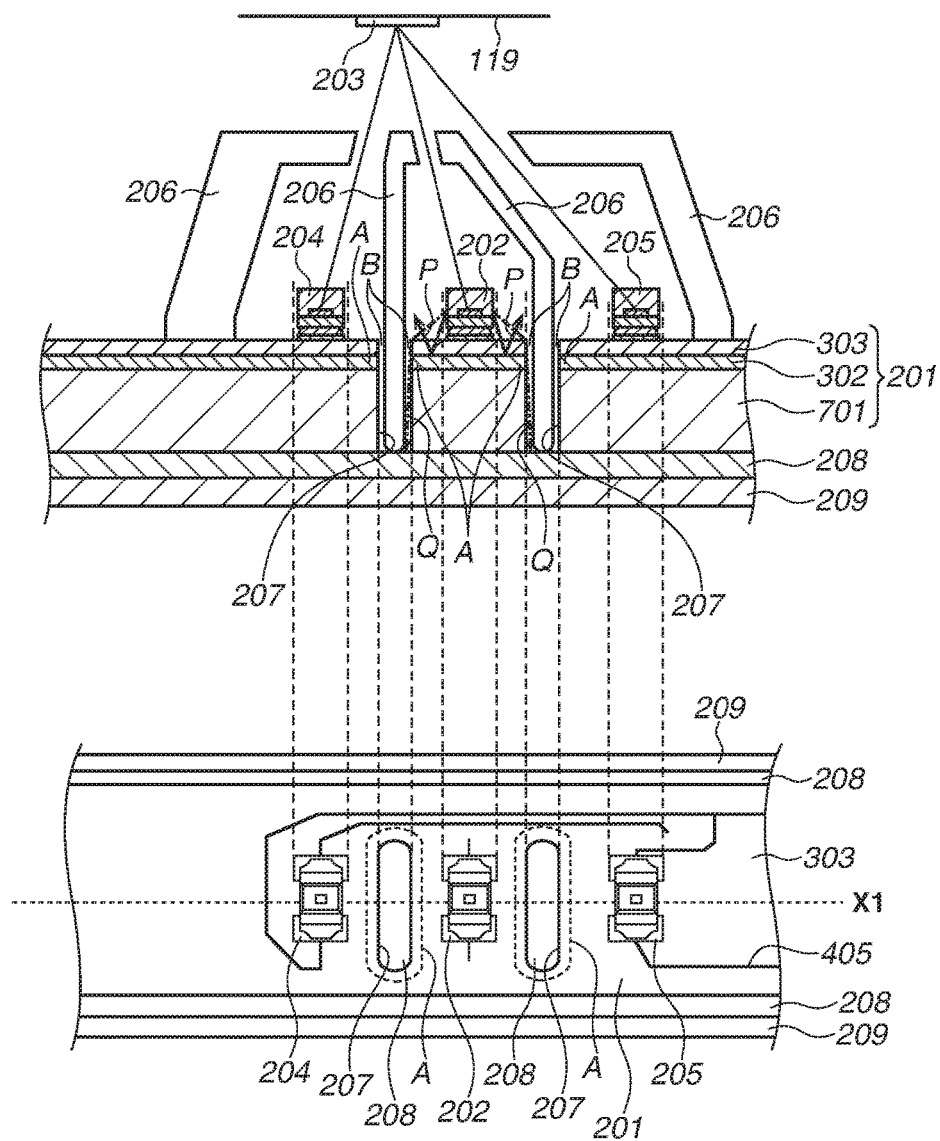
FIG. 8 illustrates a cross-sectional view (an upper part of the drawing) and an upper surface view (a lower part of the drawing) of the optical sensor unit.

FIG. 8 is a set of a cross-sectional view (an upper part of the drawing) and an upper surface view (lower part of the drawing) of the optical sensor unit 125 in a state where the light-emitting element 202 and the light-receiving elements 204 and 205 are mounted on the substrate 201 that includes the through-holes 207 formed therein and the housing 206 is attached to the substrate 201. The configuration illustrated in FIG. 8 is different from the configuration illustrated in FIG. 5 in that the copper foil layer 302 and the solder resist layer 303 are provided on only one surface of the substrate 201 and in the method for forming the through-holes 207. The region where the copper foil layer 302 is provided covers the mounting positions of the light-emitting element 202 and the light-receiving elements 204 and 205 and each region A surrounding the through-hole 207. The copper foil layer 302 extends along an inner cylindrical surface of the through-hole 207. As indicated by a path P, the light emitted from the light-emitting element 202 is reflected by the copper foil layer 302 in the region A. In other words, the copper foil layer 302 prevents the emitted light from entering the substrate layer 701. Because unnecessary light is prevented from entering the substrate layer 701, the light emitted from the light-emitting unit can be prevented from becoming disturbance light that travels in the substrate and reaching the light-receiving elements 204 and 205.

Further, as indicated by a path Q, light leaking from a clearance between the through-hole 207 and the light-shielding member 206 to the back surface of the substrate 201 is absorbed by the front surface of the spacer 208.

As mentioned above, according to the present exemplary embodiment, it is feasible to prevent the disturbance light having travelled in the substrate layer 701 from entering the light-receiving elements 204 and 205. Further, it is feasible to prevent the light leaking via the clearance between the light-shielding member 206 and the through-hole 207 from entering the light-receiving elements 204 and 205. Therefore, the optical sensor unit 125 can secure an adequate dynamic range (i.e., ratio of maximum output value to minimum output value) in the detection of the positional deviation and density variation detecting toner patch (i.e., the reference pattern) 203. When the dynamic range is maintained adequately without causing undesirable reduction, the optical sensor unit 125 can accurately detect the positional deviation and density variation detecting toner patch (i.e., the reference pattern) 203 that is formed on the surface of an image bearing member (such as the intermediate transfer member 119 or the photosensitive drum 115). More specifically, the present exemplary embodiment brings an effect of suppressing the detection accuracy of the optical sensor unit 125 from deteriorating due to the stray light.

According to the present invention, it is feasible to suppress the detection accuracy from deteriorating due to the stray light.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:
1. An optical apparatus comprising:
   a light-emitting member;
   a light-receiving member;
   a substrate, in which a substrate layer, a conductive layer and a protective layer are laminated in this order and on which the light-emitting member and the light-receiving member are mounted; and
   a light-shielding member disposed between the light-receiving member and the light-emitting member and inserted in a through-hole of the substrate provided between the light-receiving member and the light-emitting member,
   wherein the through-hole is comprised of the substrate layer, the conductive layer and the protective layer in a depth direction of the through-hole.

2. The optical apparatus according to claim 1, wherein the conductive layer is superior in terms of light-shielding property to the substrate layer.

3. The optical apparatus according to claim 1, wherein the conductive layer is exposed to an inner cylindrical surface of the through-hole.

4. The optical apparatus according to claim 1, wherein a surface of the substrate layer, a surface of the conductive layer and a surface of the protective layer form the same plane on an inner cylindrical surface of the through-hole, and the inner cylindrical surface of the through-hole is flat.

5. The optical apparatus according to claim 1, wherein the light-emitting member and the light-receiving member are bare chip elements.

6. The optical apparatus according to claim 1, wherein the substrate layer, the conductive layer and the protective layer each has a plate shape.

7. The optical apparatus according to claim 1, wherein the conductive layer is disposed around the through-hole when seen in the depth direction of the through-hole.

8. The optical apparatus according to claim 1, wherein the conductive layer is a copper layer.

9. The optical apparatus according to claim 1, wherein the substrate is a glass epoxy resin member.

10. The optical apparatus according to claim 1, wherein the light-shielding member includes a portion that covers the light-emitting member.

11. The optical apparatus according to claim 1, further comprising:
    a stay member that supports the substrate; and
    a spacer member disposed between the stay member and the substrate,
    wherein the spacer member has a counter surface that faces a back surface of the substrate having a front surface on which the light-emitting member and the light-receiving member are mounted, and the counter surface is a black surface and/or a matt finished surface.

12. The optical apparatus according to claim 11, wherein the stay member is made of metal.

13. The optical apparatus according to claim 1, wherein a toner image is formed at a portion to be irradiated with light emitted from the light-emitting member.

14. The optical apparatus according to claim 1, wherein the through-hole is formed in the substrate by performing a presswork at a portion where the conductive layer is present.

15. The optical apparatus according to claim 14, wherein the substrate is a paper phenol resin member.

16. The optical apparatus according to claim 14, wherein the conductive layer is a copper layer.

17. The optical apparatus according to claim 1, wherein the through-hole is formed in the substrate by performing a cutting work at a portion where the conductive layer is present.

18. The optical apparatus according to claim 17, wherein the substrate is a glass epoxy resin member.

19. The optical apparatus according to claim 17, wherein the conductive layer is a copper layer.

20. An image forming apparatus comprising:
    a light-emitting member;
    a light-receiving member;
    a substrate, in which a substrate layer, a conductive layer and a protective layer are laminated in this order and on which the light-emitting member and the light-receiving member are mounted; and
    a light-shielding member disposed between the light-receiving member and the light-emitting member and inserted in a through-hole of the substrate provided between the light-receiving member and the light-emitting member; and an image bearing member that carries a toner image, wherein the light-receiving member is configured to receive reflected light from the image bearing member irradiated with the light emitted from the light-emitting member, and wherein the through-hole is comprised of the substrate layer, the conductive layer and the protective layer in a depth direction of the through-hole.

\* \* \* \* \*